US010994373B2

(12) United States Patent
Milbrodt et al.

(10) Patent No.: US 10,994,373 B2
(45) Date of Patent: May 4, 2021

(54) METHOD OF LASER CUTTING A WEB STRUCTURE

(71) Applicant: Kimberly-Clark Worldwide, Inc., Neenah, WI (US)

(72) Inventors: Paul Milbrodt, Neenah, WI (US); Brian T. Anderson, New London, WI (US); Brittany Alissa Young, Fayetteville, AR (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 188 days.

(21) Appl. No.: 15/780,457

(22) PCT Filed: Dec. 5, 2016

(86) PCT No.: PCT/US2016/064899
§ 371 (c)(1),
(2) Date: May 31, 2018

(87) PCT Pub. No.: WO2017/105889
PCT Pub. Date: Jun. 22, 2017

(65) Prior Publication Data
US 2018/0345417 A1 Dec. 6, 2018

Related U.S. Application Data

(60) Provisional application No. 62/269,418, filed on Dec. 18, 2015.

(51) Int. Cl.
*B23K 26/0622* (2014.01)
*B23K 26/38* (2014.01)
*B23K 26/073* (2006.01)
*B23K 26/402* (2014.01)
*B23K 103/00* (2006.01)

(52) U.S. Cl.
CPC .......... *B23K 26/38* (2013.01); *B23K 26/0622* (2015.10); *B23K 26/073* (2013.01); *B23K 26/402* (2013.01); *B23K 2103/38* (2018.08); *B23K 2103/42* (2018.08)

(58) Field of Classification Search
CPC ............................................... B23K 26/0622
See application file for complete search history.

(56) References Cited

U.S. PATENT DOCUMENTS

| 3,338,992 | A | 8/1967 | Kinney |
| 3,341,394 | A | 9/1967 | Kinney |
| 3,485,706 | A | 12/1969 | Evans |
| 3,502,538 | A | 3/1970 | Claine |
| 3,502,763 | A | 3/1970 | Hartmann |
| 3,542,615 | A | 11/1970 | Dobo |
| 3,692,618 | A | 9/1972 | Carduck |
| 3,790,744 | A * | 2/1974 | Bowen ............... B23K 26/0006 219/121.69 |
| 3,802,817 | A | 4/1974 | Goto |
| 3,849,241 | A | 11/1974 | Butin |
| 4,340,563 | A | 7/1982 | Appel |
| 4,568,815 | A * | 2/1986 | Kimbara ............ B23K 26/0846 219/121.6 |
| 4,939,016 | A | 7/1990 | Radwanski |
| 4,959,531 | A | 9/1990 | Marino |
| 4,970,104 | A | 11/1990 | Radwanski |
| 5,158,499 | A | 10/1992 | Guckenberger |
| 6,074,097 | A | 6/2000 | Hayashi |
| 7,833,617 | B2 | 11/2010 | Kliesch |
| 8,482,713 | B2 | 7/2013 | Qi et al. |
| 2003/0057194 | A1 | 3/2003 | Fidalgo |
| 2008/0076065 | A1 | 3/2008 | Bennett |
| 2009/0242521 | A1 | 10/2009 | Alpay |
| 2011/0029124 | A1 | 2/2011 | Boyle |
| 2011/0240617 | A1 | 10/2011 | Xu |
| 2012/0021883 | A1 | 1/2012 | Callault |
| 2012/0288660 | A1 | 11/2012 | Maseiker |
| 2013/0237035 | A1 | 9/2013 | Osako |
| 2013/0264730 | A1 | 10/2013 | Wu |
| 2013/0306608 | A1 | 11/2013 | Schaefer |
| 2015/0024154 | A1 | 1/2015 | Hoerig |
| 2015/0123317 | A1 | 5/2015 | Sorem |

FOREIGN PATENT DOCUMENTS

| CN | 101203353 A | 6/2008 |
| CN | 101333771 A | 12/2008 |
| CN | 101610871 A | 12/2009 |
| CN | 103402472 A | 11/2013 |
| CN | 103648707 A | 3/2014 |
| DE | 102013212577 A1 | 12/2014 |
| EP | 0061352 A1 | 9/1982 |
| FR | 2738800 A1 | 3/1997 |
| WO | 14064562 A1 | 5/2014 |

* cited by examiner

*Primary Examiner* — Timothy Kennedy
(74) *Attorney, Agent, or Firm* — Kimberly-Clark Worldwide, Inc.

(57) ABSTRACT

A method of cutting a web structure that is utilized in the manufacture of an absorbent article. The method of cutting the web structure can employ a laser having a pulse mode of operation. In various embodiments, the frequency of the beam of radiation pulsed from the laser can be patterned to correspond to the material of the web structure. In various embodiments, the frequency of the beam of radiation pulsed from the laser can be patterned to correspond to the speed at which the web structure is moving and can change with any change in speed of the web structure movement.

11 Claims, No Drawings

METHOD OF LASER CUTTING A WEB STRUCTURE

BACKGROUND OF THE DISCLOSURE

Personal care absorbent articles are manufactured using a variety of components, including web structures, which can provide various benefits to the wearer of the absorbent article. An example of a web structure can be a liquid permeable nonwoven web or film which can be used as a body contacting layer, such as a topsheet layer, of the absorbent article. Another example of a web structure can be a liquid impermeable nonwoven web or film which can be used as a garment contacting layer, such as a backsheet layer, of the absorbent article.

Personal care absorbent articles can be manufactured in a variety of shapes such as, for example, rectangular or hourglass, and a variety of sizes which can be sized to fit a range of wearers from infant to adult. The web structures which form some of the components of an absorbent article are cut from larger sheets of web structures into the smaller, appropriately sized web structures to be incorporated into the resultant absorbent article.

The cutting of the larger sheet of web structures into the smaller, appropriately sized web structures can employ a laser which can emit a beam of radiation at the web structure. The energy output from the beam of radiation can be absorbed by the web structure in the area which is the focus of the beam of radiation. The absorption of the energy from the beam of radiation can result in the vaporization of the web structure in the area of focus. The vaporization of the web structure can result in a rough edge to the remaining web structure due to the melting of the material of the web structure which abuts the area where vaporization occurred.

As these web structures will be utilized in personal care absorbent articles and may potentially come into contact with the skin of the wearer, there is a need for a method of cutting a web structure which will result in a softer edge to the cut web structure.

SUMMARY OF THE DISCLOSURE

In various embodiments, a method of cutting a web structure can have the steps of: providing a laser capable of emitting a beam of radiation; providing the web structure wherein the web structure comprises a first portion of material and a second portion of material; directing the beam of radiation from the laser to the first portion of the web structure with a first profile of pulses per beam diameter; directing the beam of radiation from the laser to the second portion of the web structure with a second profile of pulses per beam diameter; wherein the first portion of the web structure is different from the second portion of the web structure and wherein the first profile of pulses per beam diameter is different from the second profile of pulses per beam diameter. In various embodiments, the first portion of the web structure comprises a material comprising at least one of a polyethylene, polypropylene, or polyester and the second portion of the web structure comprises a material comprising at least one of a polyethylene, polypropylene, or polyester.

In various embodiments, the first portion of web structure is a single layer of material and the second portion of the web structure is a laminate structure of at least two materials superimposed on each other. In various embodiments, the at least two materials of the laminate structure are at least partially bonded to each other.

In various embodiments, the first portion of web structure is a laminate structure of at least two layers of material superimposed on each other and the second portion of the web structure is a laminate structure of at least three layers of material superimposed on each other. In various embodiments, the at least two layers of the laminate structure of the first portion of the web are at least partially bonded to each other and wherein the at least three layers of materials of the laminate structure of the second portion of the web structure are at least partially bonded to each other.

In various embodiments, the first profile of pulses per beam diameter is from 0.25 to 32 and the second profile of pulses per beam diameter is from 0.25 to 32. In various embodiments, the first profile of pulses per beam diameter is from 0.25 to 8 and the second profile of pulses per beam diameter is from 0.25 to 8.

In various embodiments, the laser has a pulse mode of operation. In various embodiments, the laser beam of radiation is a single mode structure. In various embodiments, the laser beam of radiation has a spot diameter ranging from 150 µm to 350 µm.

In various embodiments, a method of cutting a web structure has the steps of: providing a laser; providing the web structure; moving the web structure at a first speed; directing a beam of radiation from the laser to the web structure at a first frequency resulting in a first profile of pulses per beam diameter; varying the speed of the movement of the web structure to a second speed; and directing a beam of radiation from the laser to the web structure as a second frequency resulting in a second profile of pulses per beam diameter; wherein the first frequency and the second frequency are different.

In various embodiments, the first profile of pulses per beam diameter is the same as the second profile of pulses per beam diameter. In various embodiments, the first profile of pulses per beam diameter is different from the second profile of pulses per beam diameter.

In various embodiments, the first profile of pulses per beam diameter is from 0.25 to 32 and the second profile of pulses per beam diameter is from 0.25 to 32. In various embodiments, the first profile of pulses per beam diameter is from 0.25 to 8 and the second profile of pulses per beam diameter is from 0.25 to 8.

In various embodiments, the laser has a pulse mode of operation. In various embodiments, the laser beam of radiation is a single mode structure. In various embodiments, the laser beam of radiation has a spot diameter ranging from 150 µm to 350 µm.

In various embodiments, the web structure comprises a material comprising at least one of a polyester, polypropylene, or polyethylene.

DETAILED DESCRIPTION OF THE DISCLOSURE

The current disclosure is directed towards a method of cutting a web structure that is utilized in the manufacture of an absorbent article. The method of cutting the web structure can employ a laser having a pulse mode of operation. In various embodiments, the frequency of the beam of radiation pulsed from the laser can be patterned to correspond to the material of the web structure. In various embodiments, the frequency of the beam of radiation pulsed from the laser can be patterned to correspond to the speed at which the web structure is moving and can change with any change in speed of the web structure movement.

Definitions

The term "absorbent article" refers herein to an article which may be placed against or in proximity to the body (i.e., contiguous with the body) of the wearer to absorb and contain various liquid, solid, and semi-solid exudates discharged from the body. Such absorbent articles are intended to be discarded after a limited period of use instead of being laundered or otherwise restored for reuse. It is to be understood that the present disclosure is applicable to various disposable absorbent articles, including, but not limited to, diapers, training pants, youth pants, swim pants, feminine hygiene products, including, but not limited to, menstrual pads, incontinence products, medical garments, surgical pads and bandages, other personal care or health care garments, and the like without departing from the scope of the present disclosure.

The term "bonded" refers herein to the joining, adhering, connecting, attaching, or the like, of two elements. Two elements will be considered bonded together when they are joined, adhered, connected, attached, or the like, directly to one another or indirectly to one another, such as when each is directly bonded to intermediate elements. The bonding of one element to another can occur via continuous or intermittent bonds. The bonding of one element to another can occur via any suitable means such as, but not limited to, adhesives, ultrasonic bonds, thermal bonds, pressure bonds, or other conventional techniques. An adhesive can be applied continuously or intermittently as beads, a spray, parallel swirls, or the like. Suitable adhesives can be obtained from Bostik Findlay Adhesives, Inc. of Wauwatosa, Wis., U.S.A.

The term "carded web" refers herein to a web containing natural or synthetic staple length fibers typically having fiber lengths less than about 100 mm. Bales of staple fibers can undergo an opening process to separate the fibers which are then sent to a carding process which separates and combs the fibers to align them in the machine direction after which the fibers are deposited onto a moving wire for further processing. Such webs are usually subjected to some type of bonding process such as thermal bonding using heat and/or pressure. In addition to or in lieu thereof, the fibers may be subject to adhesive processes to bind the fibers together such as by the use of powder adhesives. The carded web may be subjected to fluid entangling, such as hydroentangling, to further intertwine the fibers and thereby improve the integrity of the carded web. Carded webs, due to the fiber alignment in the machine direction, once bonded, will typically have more machine direction strength than cross machine direction strength.

The term "film" refers herein to a thermoplastic film made using an extrusion and/or forming process, such as a cast film or blown film extrusion process. The term includes apertured films, slit films, and other porous films which constitute liquid transfer films, as well as films which do not transfer fluids, such as, but not limited to, barrier films, filled films, breathable films, and oriented films.

The term "fluid entangling" and "fluid entangled" refers herein to a formation process for further increasing the degree of fiber entanglement within a given fibrous nonwoven web or between fibrous nonwoven webs and other materials so as to make the separation of the individual fibers and/or the layers more difficult as a result of the entanglement. Generally this is accomplished by supporting the fibrous nonwoven web on some type of forming or carrier surface which has at least some degree of permeability to the impinging pressurized fluid. A pressurized fluid stream (usually multiple streams) can then be directed against the surface of the nonwoven web which is opposite the supported surface of the web. The pressurized fluid contacts the fibers and forces portions of the fibers in the direction of the fluid flow thus displacing all or a portion of a plurality of the fibers towards the supported surface of the web. The result is a further entanglement of the fibers in what can be termed the Z-direction of the web (its thickness) relative to its more planar dimension, its X-Y plane. When two or more separate webs or other layers are placed adjacent one another on the forming/carrier surface and subjected to the pressurized fluid, the generally desired result is that some of the fibers of at least one of the webs are forced into the adjacent web or layer thereby causing fiber entanglement between the interfaces of the two surfaces so as to result in the bonding or joining of the webs/layers together due to the increased entanglement of the fibers. The degree of bonding or entanglement will depend on a number of factors including, but not limited to, the types of fibers being used, the fiber lengths, the degree of pre-bonding or entanglement of the web or webs prior to subjection to the fluid entangling process, the type of fluid being used (liquids, such as water, steam or gases, such as air), the pressure of the fluid, the number of fluid streams, the speed of the process, the dwell time of the fluid and the porosity of the web or webs/other layers and the forming/carrier surface. One of the most common fluid entangling processes is referred to as hydroentangling which is a well-known process to those of ordinary skill in the art of nonwoven webs. Examples of fluid entangling process can be found in U.S. Pat. No. 4,939,016 to Radwanski et al., U.S. Pat. No. 3,485,706 to Evans, and U.S. Pat. Nos. 4,970,104 and 4,959,531 to Radwanski, each of which is incorporated herein in its entirety by reference thereto for all purposes.

The term "gsm" refers herein to grams per square meter.

The term "hydrophilic" refers herein to fibers or the surfaces of fibers which are wetted by aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by Cahn SFA-222 Surface Force Analyzer System, or a substantially equivalent system. When measured with this system, fibers having contact angles less than 90 are designated "wettable" or hydrophilic, and fibers having contact angles greater than 90 are designated "nonwettable" or hydrophobic.

The term "liquid impermeable" refers herein to a layer or multi-layer laminate in which liquid body exudates, such as urine, will not pass through the layer or laminate, under ordinary use conditions, in a direction generally perpendicular to the plane of the layer or laminate at the point of liquid contact.

The term "liquid permeable" refers herein to any material that is not liquid impermeable.

The term "meltblown" refers herein to fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which can be a microfiber diameter. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin et al., which is incorporated herein by reference. Meltblown fibers are microfibers which may be continuous or discontinuous, are generally smaller than about 0.6 denier, and may be tacky and self-bonding when deposited onto a collecting surface.

The term "nonwoven" refers herein to a material which is formed without the aid of a textile weaving or knitting process. The material can have a structure of individual fibers, filaments, or threads (collectively referred to as "fibers") which can be interlaid, but not in an identifiable manner as in a knitted fabric. Nonwoven material can be formed from many processes such as, but not limited to, meltblowing processes, spunbonding processes, carded web processes, etc.

The term "spunbond" refers herein to small diameter fibers which are formed by extruding molten thermoplastic material as filaments from a plurality of fine capillaries of a spinnerette having a circular or other configuration, with the diameter of the extruded filaments then being rapidly reduced by a conventional process such as, for example, eductive drawing, and processes that are described in U.S. Pat. No. 4,340,563 to Appel et al., U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Peterson, and U.S. Pat. No. 3,542,615 to Dobo et al., each of which is incorporated herein in its entirety by reference. Spunbond fibers are generally continuous and often have average deniers larger than about 0.3, and in an embodiment, between about 0.6, 5 and 10 and about 15, 20 and 40. Spunbond fibers are generally not tacky when they are deposited on a collecting surface.

The term "thermoplastic" refers herein to a material which softens and which can be shaped when exposed to heat and which substantially returns to a non-softened condition when cooled.

The term "wearer" refers herein to one who uses an absorbent article, such as, but not limited to, a diaper, training pant, youth pant, incontinent product, feminine napkin, or other absorbent article and the absorbent article is placed in proximity to the body to capture body exudates.

Web Structure:

While the embodiments described herein may generally apply to a web structure processed in the longitudinal direction of the web structure, also known as the machine direction, it should be noted that one of ordinary skill could apply the information herein to a web structure processed in the transverse direction of the web structure, also known as the cross direction, without departing from the spirit and scope of the disclosure.

In various embodiments, the web structure can be a single layer of material. In various embodiments, the web structure can have a laminate structure in which at least two layers of material are superimposed on each other. In various embodiments, the web structure can have a laminate structure in which at least three layers of material are superimposed on each other. In various embodiments, a web structure can have a laminate structure in which at least four layers of material are superimposed on each other. In various embodiments, a portion of the web structure can be a single layer of material and another portion of the same web structure can be a laminate structure in which at least two layers of material are superimposed on each other. In various embodiments, a portion of the web structure can be a laminate structure in which at least two layers of material are superimposed on each other and another portion of the same web structure can be a laminate structure in which at least three layers of material are superimposed on each other. In various embodiments, the layers of a laminate structure can be at least partially bonded to each other. In various embodiments, the layers of a laminate structure are fully bonded to each other. In various embodiments, the layers of a laminate structure are not bonded to each other.

A layer of the web structure can be manufactured from a wide selection of materials, such as synthetic fibers (for example, polyester or polypropylene fibers), natural fibers (for example, wood or cotton fibers), a combination of natural and synthetic fibers, porous foams, reticulated foams, film, apertured plastic films, or the like. Examples of suitable materials include, but are not limited to, rayon, wood, cotton, polyester, polypropylene, polyethylene, nylon, or other heat-bondable fibers, bicomponent staple fibers, polyolefins, such as, but not limited to, copolymers of polypropylene and polyethylene, linear low-density polyethylene, and aliphatic esters such as polylactic acid, finely perforated film webs, net materials, and the like, as well as combinations thereof. An example of a bicomponent staple fiber includes a polyethylene/polypropylene bicomponent fiber. In this particular bicomponent fiber, the polypropylene forms the core and the polyethylene forms the sheath of the fiber. Bicomponent fibers having other orientations, such as multi-lobe, side-by-side, or end-to-end, may be used without departing from the scope of this disclosure.

The material forming the layer can be processed into a nonwoven web or a film. The nonwoven web or film, therefore, forms a layer of a web structure. Examples of a nonwoven web can include spunbond web, meltblown web, coform web, carded web, bonded-carded web, bicomponent spunbond web, spunlace, or the like, as well as combinations thereof.

A layer of the web structure can be composed of a substantially hydrophobic material, and the hydrophobic material can, optionally, be treated with a surfactant or otherwise processed to impart a desired level of wettability and hydrophilicity. The surfactant can be applied by any conventional means, such as spraying, printing, brush coating or the like. The surfactant can be applied to the entire layer of a web structure or it can be selectively applied to particular sections of the layer of a web structure.

The web structure can be elastic or non-elastic, stretchable or non-stretchable. In various embodiments, the web structure can be suitably stretchable, and more suitably elastic, in at least the transverse direction. In various embodiments, the web structure can be stretchable, and more suitably elastic, in both the transverse and the longitudinal directions.

The web structure can be breathable, liquid permeable and/or liquid impermeable. In various embodiments, the web structure can be a single liquid permeable layer. In various embodiments, the web structure can be a single liquid impermeable layer. In various embodiments, the web structure can have a laminate structure in which at least two layers of material are superimposed on each other and at least one of the layers is liquid impermeable. In various embodiments, the web structure can have a laminate structure in which at least two layers of material are superimposed on each other and the web structure is breathable and liquid impermeable.

In various embodiments, a layer of a web structure can have a basis weight from about 10, 12 or 15 gsm to about 20, 22, 25 or 30 gsm. In various embodiments, a layer of a web structure can be a meltblown web of polyolefin fibers. In various embodiments, a layer of a web structure can be a spunbond web of polyolefin fibers. An example of such a layer of a web structure can be a 20 gsm spunbond polypropylene nonwoven web. In various embodiments, a layer of a web structure can be a bonded-carded web of natural and/or synthetic fibers. An example of such a layer of a web structure can be a 100% polypropylene bonded-carded web with a diamond bond pattern available from Sandler A.G., Germany, such as 30 gsm Sawabond 4185® or equivalent. In various embodiments, a layer of a web structure can be a nonwoven bicomponent web. The nonwoven bicomponent web can be a spunbond bicomponent web or a bonded-carded bicomponent web. In various embodiments a layer of a web structure can be a film. In various embodiments, the web structure can be a microporous polymeric film such as polyethylene or polypropylene. An example of a film layer can be a 19 gsm Berry Plastics XP-8695H film or equivalent commercially available from Berry Plastics Corporation, Evansville, Ind., U.S.A. Another example of such a layer of a web structure can be a 22 gsm polyethylene film. In various embodiments, a web structure can have a laminate structure in which three layers of material have been superimposed on each other. An example of such an embodiment can be a laminate structure in which the three layers of material of the laminate structure can be a spunbond-meltblown-spunbond laminate structure having 10% meltblown content applied between the two spunbond layers. In various embodiments, the web structure can have a laminate structure in which four layers of material have been superimposed on each other. An example of such an embodiment can be a laminate structure in which the four layers of material of the laminate structure can be spunbond-spunbond-film-spunbond.

The web structure utilized as a component of an absorbent article is cut and separated from a larger web structure. The cutting step in the manufacturing process can employ a laser such as described herein. The web structure has two major surfaces, one which faces the laser and an opposing surface which faces away from the laser. In order to effect a proper cut line wherein the absorbent article component web structure can be cleanly separated from the primary web structure, the laser beam cuts through the web structure from the facing major surface of the web structure to the opposing major surface of the web structure. The cut line is a result of the disruption of the molecules which form the web structure in the area which is the focus of the laser. To be receptive to the energy emitted from the laser the web structure will have an absorption spectra. In various embodiments, the absorption spectra of the web structure having a single layer of material is the same as the absorption spectra of the single layer of material. In various embodiments, the absorption spectra of a web structure having a laminate structure in which at least two layers of material are superimposed on each will be a compilation of the absorption spectra of each of the individual layers of the laminate structure of the web structure. In various embodiments, a web structure having a portion which is single layer of material and another portion having a laminate structure (or a web structure having two separate portions which are of differing laminate structures) will have portions of the same web structure with differing absorption spectra. The absorption of laser energy by each layer of the web structure follows Beers Law. In various embodiments, each layer of the web structure absorbs at least 60% of the laser energy when the laser penetrates through the layer of the web structure.

Laser Cutting:

A laser is a device which emits a powerful, concentrated beam of light. The beam of light is stimulated, amplified, electromagnetic radiation and is made up of light waves which are coherent, i.e., in phase, and monochromatic, i.e., of the same wavelength. Each laser is usually named according to the particular lasing medium which it employs, and, depending on the particular atomic structure of that medium, each laser emits its own specific and characteristic wavelength, i.e., one of a well-defined frequency. Laser wavelengths can range from about 0.2 to about 40 microns and their frequencies can range from about $1.5 \times 10^{15}$ to about $0.75 \times 10^{13}$ cycles per second. Examples of several types of lasers available for use are: gaseous lasers such as carbon dioxide or helium-neon; solid state light pumped lasers such as ruby, neo-dymium-yttrium aluminum garnet (Nd-YAG), or glass; semi-conductor lasers such as gallium arsenide, and plastic lasers and lasers using conjugated organic molecules such as benzene, toluene or naphthalene.

Laser beams transport great energy. The power available from such energy can range from a fraction of a watt to many thousand watts. Generally, the beam power used can be varied depending on the thickness of the web structure. In various embodiments, the beam power can be from about 2 to 50 or 100 watts. The intensity of the energy, i.e., the amount that flows per second across a unit area of material perpendicular to the beam, can be varied and controlled by, for example, varying the focus of the beam according to various known methods.

The energy of a laser beam is transported according to the output pattern or mode structure of the beam. A beam can have a single mode or multimode structure. A beam of single mode output has all of its energy in a single hot spot with an intensity distribution that follows a Gaussian curve when the intensity points are taken along a line perpendicular to the axis of the beam. A multimode beam is comprised of a series of rings and/or spots symmetrical about the beam axis. The single mode beam can be focused to a smaller spot diameter than the multimode beam and such a spot has very high intensity. In various embodiments, a laser having a single mode structure and whose beam is focusable to a small spot size or diameter is most suitable for the method described herein. A small spot size for the laser beam can be desirable because energy therein contained is so concentrated that a small, precise volume of web structure can be rapidly heated, vaporized or otherwise degraded in manner that effects a clean cut without affecting adjacent areas of the web structure. In various embodiments, the laser spot diameter can range from about 150 or 200 µm to about 250, 300 or 350 µm. In various embodiments, the laser spot diameter is about 250 µm.

The laser beam can be focused with suitable focusing optics and controlled to suitable power levels to accomplish the vaporization along a narrow cut line. The diameters of the spot to which a laser beam is focused to effect a satisfactory cut line according to this disclosure can be of any suitable dimension, depending, inter alia, on the thickness of the web structure. Any suitable lens capable of focusing a beam of laser radiation can be used with the laser. In various embodiments, lenses having short focal lengths can be utilized to provide the desired small spot sizes. A variety of materials known to the art are available for use as such lenses depending on the wavelength to be transmitted therethrough. For example, germanium, gallium arsenide, or sodium chloride lenses can be used with a carbon dioxide laser.

Laser beams can be of two types, pulsed and continuous. The former involves short, relatively high powered pulses or emissions which can span, for peak pulses, from about 15 nanoseconds to about 1 millisecond, and for standard control pulses, from about 1 millisecond to greater than 1 second. In various embodiments, a laser emitting pulsed beams of energy is suitable for the method described herein. The frequency of the beam of radiation pulsed from the laser is selected dependent upon the type of material in the layers of the web structure. The frequency of the beam of radiation pulsed from the laser is also selected dependent upon the cut speed. In various embodiments, the frequency can from about 2, 5, 7, 10, 15, 20, 22, 25, 30, 35, 40, 45, 47, or 50 to about 55, 60, 63, 65, 0, 75, 80, 85, 90, 95, or 100 kHz. In various embodiments, the cut speed can be from about 100, 150, 200, or 250 in/sec to about 300, 350, 400, 450, 500, 550, 600 or 650 in/sec. In various embodiments, the line speed can be from about 400, 450, 500 or 750 ft/min to about 1000, 1250, 1350, 1500, 1600, 1700, 1800 or 1900 ft/min. The frequency of the beam of radiation pulsed from the laser can result in a profile of the number of pulses per laser beam diameter. In various embodiments, the profile of the number of pulses per laser beam diameter can range from 0.25, 1, 1.5, 2, or 4 to 6, 8, or 32. In such embodiments, a consecutive pulse can overlap with at least the immediately preceding pulse in the web structure. The overlap of pulses can create an increase in the temperature in the area of web structure which is the focus of the laser beam. This increase in temperature can result in the area of the web structure being vaporized or ablated away before potentially damaging quantities of heat propagate into the remaining edge portions of the remaining web structure. As will be described herein, the frequency can be varied with the cut speed to provide a consistent number of pulses per unit of cut length.

The wavelength of the laser beam can be a wavelength whose relationship to the absorptive spectra of the layer(s) of the web structure is such that it will be absorbed in the layer(s) of the web structure in a manner that will effect a suitable cut line in the web structure. The laser radiation can be selected to have a wavelength at which a layer of the web structure has substantial absorption so that the absorbed electromagnetic radiation can effectively vaporize or ablate the web structure along the cut line. Otherwise, the laser radiation would be transmitted or reflected by the layer of the web structure just as other incident light, whose wavelength is within an intended operating range of the web structure. In various embodiments, a laser has a fixed wavelength and can be one of 9.3, 10.1, 10.2, 10.3, or 10.6 μm. In various embodiments, a laser has a fixed wavelength of 10.2 μm.

When there is relative movement along a predetermined path between a laser beam of a particular wavelength and a web structure partly transparent to that wavelength, energy the width of the diameter of the beam and more concentrated at its center, is absorbed into the web structure. As the energy is absorbed it is transformed into heat which softens and melts the web structure along the beam path. Toward the center of the beam path where the intensity is greater, some of the web structure molecules are vaporized and the resulting expanding gases form the cut line in the web structure. If the molecules that are vaporized are at the surface of the web structure, their gases leave cavities as they rise directly into the atmosphere. If the vaporized molecules are not on the surface, their gases form bubbles which rise through, blow out, or even, if the energy density is great enough, explode through surrounding and/or overlying melted web structure. As the expanding bubbles form and rise, they mechanically move molten material out of the way. Under proper conditions, e.g., when a beam of sufficient intensity is subjected to a web structure for a sufficient time, enough molecules are vaporized along a line such that resulting bubbles merge, coalesce, or otherwise cooperate to form a cut line. The web structure moved by the bubbles forms a slightly protruding bead along the surface of each of the cut line's upper longitudinal edges. Although most of the bubbles which form the cut line result from vaporization of the web structure, some bubble sites apparently result from hot spots caused by highly absorbent impurities such as dirt or metals and from entrapped moisture or gases normally present for example in molecular lattice structures and grain boundaries of the web structure. The size and distribution of bubbles occurring in a web structure depend on several factors including the intensity of the beam, the time it impinges an area of the web structure and the characteristics of the web structure itself.

Where vaporization of molecules occurs in a web structure, i.e., at its surface or within its thickness, depends on the coefficient of absorption as applied in the exponential absorption law and on the thermal diffusivity and conductivity of the web structure. Vaporization will first occur mostly at or near the incident surface and will proceed downward incrementally into materials of the web structure having high coefficient of absorption, whereas it will occur fairly uniformly through the thickness of those having a low coefficient of absorption.

In various embodiments, it can be desirable to maintain the profile of the number of pulses per beam diameter constant. Maintaining the profile of the number of pulses per beam diameter constant can provide for a less rough edge to the remaining web structure following the cutting by the laser beam. In various embodiments, when a web structure is moving at a constant speed the profile of the number of pulses per beam diameter can be maintained as a constant by not varying the frequency of the beam of radiation pulsed from the laser (i.e., a "steady state"). In various embodiments, it may be desirable to alter the speed of movement of the web structure. Examples of such time periods include start-up and shut-down of the manufacturing equipment. In current commercial processes, during such time frames of start-up and shut-down the laser is generally profiled to the "steady state" of number of pulses per beam diameter and the web structure cut during start-up and shut-down may be deemed not suitable for the absorbent article which results in waste. To minimize this waste of web structure that may have rough edges due to the laser cutting it is desirable to have a laser which can also experience variation in the frequency of the beam of radiation pulsed from the laser in order to maintain a constant number of pulses per beam diameter. In such embodiments, maintaining a constant number of pulses per beam diameter may involve increasing or decreasing the frequency of pulses of the beam pulsed from the laser. For example, in various embodiments, it may be desirable to increase the speed of movement of the web structure and to maintain the profile of the number of pulses in a beam diameter, the frequency of the beam of radiation pulsed from the laser will need to correspondingly increase with the increase in the speed of movement of the web structure. In various embodiments, it may be desirable to decrease the speed of movement of the web structure and to maintain the profile of the number of pulses in a beam diameter, the frequency of the beam of radiation pulsed from the laser will need to correspondingly decrease with the decrease in the speed of movement of the web structure. In various embodiments, it may be desirable to utilize the laser to cut a web structure having a portion with a layer structure that can be different than a layer structure of another portion of the same web structure. In such embodiments, the profile of the number of pulses per beam diameter in the two portions may not be the same to result in a softer edge of the remaining web structure. For example, a web structure may have a portion which is a single layer of material and the same web structure may have another portion which has at least two layers of material bonded together. In such embodiments, the laser can be programmed to cut each portion relative to their absorptive spectra which can result in a profile of the number of pulses per beam diameter varying between the two portions. For example, the laser can be used to cut a first portion of a web structure formed of a single layer of material which has an absorptive spectra and a second portion of the web structure which has a laminate structure of at least two layers of material bonded together and its own absorptive spectra. When cutting this web structure, the profile of the number of pulses per beam diameter in the first portion can be different than the profile of the number of pulses per beam diameter in the second portion.

In various embodiments, it may be desirable to alter the speed of movement of a web structure in which first portion of the web structure is different from a second portion of the same web structure. In such embodiments, the frequency of the beam of radiation pulsed from the laser may change as the speed of movement of the web structure changes. In such embodiments, as the web structure can also differ from one portion to another, the profile of the number of pulses in a beam diameter may also differ between the portions of the web structure.

When introducing elements of the present disclosure or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements. Many modifications and variations of the present disclosure can be made without departing from the spirit and scope thereof. Therefore, the exemplary embodiments described above should not be used to limit the scope of the invention.

What is claimed is:

1. A method of cutting a web structure, the method comprising the steps of: providing a laser; providing the web structure wherein the web structure comprises a first portion comprising at least one layer of material and a second portion comprising at least two layers of material, wherein the number of layers in the first portion and the second portion are different; directing a the beam of radiation from the laser to the first portion of the web structure with a first profile of pulses per beam diameter; directing the beam of radiation from the laser to the second portion of the web structure with a second profile of pulses per beam diameter; wherein the first portion of the web structure is different from the second portion of the web structure and wherein the first profile of pulses per beam diameter is different from the second profile of pulses per beam diameter.

2. The method of claim 1 wherein the first portion of the web structure comprises a material comprising at least one of a polyethylene, polypropylene, or polyester and the second portion of the web structure comprises a material comprising at least one of a polyethylene, polypropylene, or polyester.

3. The method of claim 1 wherein the first portion of web structure is a single layer of material and the second portion of the web structure is a laminate structure of at least two materials superimposed on each other.

4. The method of claim 3 wherein the at least two materials of the laminate structure are at least partially bonded to each other.

5. The method of claim 1 wherein the first portion of web structure is a laminate structure of at least two layers of material superimposed on each other and the second portion of the web structure is a laminate structure of at least three layers of material superimposed on each other.

6. The method of claim 5 wherein the at least two layers of the laminate structure of the first portion of the web are at least partially bonded to each other and wherein the at least three layers of materials of the laminate structure of the second portion of the web structure are at least partially bonded to each other.

7. The method of claim 1 wherein the first profile of pulses per beam diameter is from 0.25 to 32 and the second profile of pulses per beam diameter is from 0.25 to 32.

8. The method of claim 7 wherein the first profile of pulses per beam diameter is from 0.25 to 8 and the second profile of pulses per beam diameter is from 0.25 to 8.

9. The method of claim 1 wherein the laser has a pulse mode of operation.

10. The method of claim 1 wherein the laser beam of radiation is a single mode structure.

11. The method of claim 1 wherein the laser beam of radiation has a spot diameter ranging from 150 μm to 350 μm.

* * * * *